United States Patent [19]

Kriesel et al.

[11] Patent Number: 5,484,410
[45] Date of Patent: Jan. 16, 1996

[54] MIXING AND DELIVERY SYSTEM

[75] Inventors: Marshall S. Kriesel, St. Paul; Thomas N. Thompson, Richfield, both of Minn.

[73] Assignee: Science Incorporated, Bloomington, Minn.

[21] Appl. No.: 362,842

[22] Filed: Dec. 22, 1994

Related U.S. Application Data

[63] Continuation-in-part of Ser. No. 989,097, Feb. 1, 1993, Pat. No. 5,385,546, which is a continuation-in-part of Ser. No. 903,651, Jun. 24, 1992, Pat. No. 5,385,545.

[51] Int. Cl.[6] ................................................. A61M 37/00
[52] U.S. Cl. .............................. 604/89; 604/82; 604/91; 604/92; 604/56; 604/410; 604/416
[58] Field of Search ................................ 604/56, 82–84, 604/87, 89, 91–92, 410, 416, 905

[56] References Cited

U.S. PATENT DOCUMENTS

2,105,946  1/1938  Lewis ........................................ 604/82
3,889,674  6/1975  Cilento ...................................... 604/56
4,432,755  2/1984  Pearson ..................................... 604/56

Primary Examiner—Randall L. Green
Assistant Examiner—P. Zuttarelli
Attorney, Agent, or Firm—J. E. Brunton

[57]  ABSTRACT

An apparatus for separately storing a first component, such as a drug and for mixing this first component with a second component, such as a sterilized diluent, to form a beneficial agent which can be delivered to a patient from the container containing the second component. The device includes novel means for interconnecting a container, such as a glass vial containing a first component, such as a drug, with a second container such as a flexible bag containing the second component such as a parenteral liquid, and then for controllably ejecting the first component from the glass vial so that it will fall by force of gravity into the second container whereby the first and second components will thoroughly mix under sterile conditions.

20 Claims, 8 Drawing Sheets

MIXING AND DELIVERY SYSTEM

BACKGROUND OF THE INVENTION

This is a Continuation In Part application of application Ser. No. 07/989,097 filed Feb. 1, 1993, now U.S. Pat. No. 5,385,546 which is a Continuation In Part of application, Ser. No. 07/903,651, filed Jun. 24, 1992, now U.S. Pat. No. 5,385,545.

FIELD OF THE INVENTION

The present invention relates generally to component mixing. More particularly, the invention concerns an apparatus for separately storing a first component, such as a drug and for mixing this first component with a second component, such as a sterilized diluent, to form a beneficial agent which can be delivered to a patient from the container containing the second component. The device includes novel means for interconnecting a container, such as a glass vial containing the first component, with a flexible bag containing the second component and then for mixing the components under sterile conditions.

DISCUSSION OF THE INVENTION

In the past, pharmaceuticals have been provided by drug manufacturers in sterilized vials, typically of glass construction. When the pharmaceuticals are in powder form, they are generally administered to the patient within a carrier liquid by standard intravenous procedures. Such carrier liquids include saline solution, dextrose solution and sterilized water.

Mixing of the powdered pharmaceuticals with the carrier liquid has been accomplished in several ways many of them being quite crude. For example, a common practice is to inject a quantity of the liquid carrier into the vial to dissolve the powdered component. Then using a cannula and syringe, the solution thus formed is injected into a larger container such as a flexbag containing the liquid carrier. This method is quite tedious and provides substantial opportunities for contamination and error.

In those instances where the pharmaceutical must be diluted before delivery to a patient, as is the case with powdered pharmaceuticals, the pharmaceutical can also be injected directly into a container of diluent and the container then interconnected with a suitable administration set for intravenous delivery of the solution to a patient. As a general rule, the diluent is packaged in glass bottles, or flexible plastic containers such as those sold under the names MINI-BAG™ and VIAFLEX® by Travenol Laboratories, Inc. of Deerfield, Ill. These containers are conveniently provided with administration ports for connection to the administration set which delivers the container contents from the container to the patient. The pharmaceutical is typically added to the container through some type of an inlet port or vial receptacle provided on the container.

Because infusion of medicaments is most often accomplished in a hospital environment, it is the nurse, doctor or medical technician who mixes the drug and diluent usually at one time shortly before administration of the drug to the patient. This mixing step can be time consuming and hazardous, as for example, when toxic drugs are involved. Further, since many of the prior art mixing devices are crude and imprecise, accurate, sterile and thorough mixing of the drug and the diluent is most difficult and time consuming. Accordingly, such devices are not well suited for use in the home environment.

Several types of closed drug delivery systems which are somewhat more sophisticated have recently been made available. These systems typically comprise a flexible container such as a plastic bag to which a glass drug vial can be easily coupled. The flexible container usually contains a liquid diluent and often includes a frangible member that allows fluid passage only when broken. As a general rule, when the drug vial is coupled with the flexible container, the stopper of the drug vial is pierced and the frangible member ruptured so as to allow sterile communication between the drug vial and the liquid diluent contents of the flexible container. Mixing of the drug with the diluent is accomplished by manipulation of the flexible container. Exemplary of prior art systems of this character are those disclosed in U.S. Pat. No. 4,583,971 issued to Bocquet, et al. and in U.S. Pat. No. 4,606,734 issued to Lyons. The Lyons apparatus includes a compressible chamber with a liquid component therein, the compressible chamber including gas trapping and reservoir compartments in open communication. The gas trapping compartment can be connected to a container such as a drug vial having a mixing component therein. After a pathway between the vial and the gas trapping compartment is opened, mixing is accomplished through manipulation of the compressible chamber.

Another very successful prior art, dual container system is described in U.S. Pat. No. 4,614,267 issued to Larkin and U.S. Pat. No. 4,614,515 issued to Tripp and Larkin. In this system, a flexible diluent container includes a tubular port which provides means for securing thereto a stoppered medicament vial as well as a stopper removal means. The stopper removal means includes an engagement element, or extractor, which is attached to a removable cover and seals the inner end of the port. In use, as the vial is advanced into the tubular port, the vial stopper moves into engagement with the extractor which grips the stopper enabling it to be pulled from the vial as the cover is pulled from the port. Once the stopper has been removed from the vial, the powdered contents of the vial, such as a lyophilized drug, can be dumped into the diluent in the bag and mixed therewith through manipulation of the bag.

Still another type of component mixing device is disclosed in U.S. Pat. No. 4,467,588 issued to Carveth. The Carveth device includes two sealed chambers having a frangible sterilized connection therebetween. One chamber carries the liquid component and the other carries a sealed vial containing the second component. The frangible connection provides a sterile pathway for intermixing the components.

The devices of the present invention comprise improvements upon the devices disclosed in co-pending application, Ser. No. 07/989,097, and offer numerous advantages over the prior art devices by providing a closed system for separately storing and selectively intermixing a wide variety of different types of medicaments and other beneficial agents with a diluent or other parenteral fluid under completely sterile conditions. Co-pending application, Ser. No. 07/989,097 filed Feb. 1, 1993, is incorporated herein by reference as though fully set forth herein. As will become apparent from the discussion which follows, the present application expands on the inventive concept set forth in application Ser. No. 07/989,097, and, accordingly, this earlier-filed application should be referred to to obtain a complete understanding of the extent of the novel improvements described herein. Reference should also be made to Ser. No. 07/989,097 for a definition of many of the terms used in the present application.

SUMMARY OF THE INVENTION

The apparatus of the present invention is used for intermixing first and second components and includes a flexible container having a fluid reservoir for containing a liquid component, such as a diluent. In fluid communication with the reservoir is an inlet port into which the assembly containing the first component, such as a beneficial agent, can be introduced. The assembly carrying the beneficial agent includes a support structure to which the beneficial agent is removably affixed and a housing, such as a glass vial, which serves to contain the support structure within a sealed, sterile environment. Following mating of the assembly carrying the beneficial agent with the flexible container, the beneficial agent is exposed to the fluid contained within the fluid reservoir. During the mixing operation, the fluid within the reservoir flows through and about the substrate in a manner such that the beneficial agent, removably carried thereby, is separated from the substrate and thoroughly intermixed with the fluid to form the solution to be delivered to the patient via an administration set that is connected to the flexible container.

It is an object of the present invention to provide an apparatus of the character described in the preceding paragraph which provides the opportunity to add to a diluent or other parenteral fluid contained within a flexible solution container (flexbag), selected elements, chemical compounds and biologically active materials, including drugs, medicaments, biological agents, and other therapeutic agents (additives).

Another object of the invention is to provide an apparatus of the character described in which the adding means, including the substrate which carries the first component, or additive, is maintained within a completely sterile environment, such as a sealed or stoppered glass vial, until immediately prior to the controlled mixing of the first and second components.

Another object of the invention is to provide an apparatus of the class described in which a wide variety of selected additives can be removably affixed to the substrate that is controllably exposed to the liquid contained within the fluid reservoir of the flexbag assembly.

Another object of the invention is to provide a device of the aforementioned type in which toxic or other hazardous compounds, including those with short therapeutic lives can be separately and safely stored until immediately prior to their use following being intermixed with the liquid compound contained within the separate flexible bag container.

Another object of the invention is to provide a device of the character described in the preceding paragraph in which toxic or other hazardous compounds which are to be intermixed with the liquid component can be separately and safely handled during the manufacture of the substrate portion of the device and in which the substrate carrying the hazardous materials can, following manufacture, be safely stored within a sealed glass vial until time of use.

Another object of the invention is to provide a device of the class described in which the additive or beneficial agent components, such as a drug, can be uniformly deposited or otherwise removably affixed to the additive support in a manner to maximize immediate and substantially complete separation of the additive and complete intermixing thereof with the liquid component.

Still another object of the invention is to provide a device of the character described in the preceding paragraphs which is easy to use, is highly reliable, and is inexpensive to produce in quantity so that the device can be disposed of after use.

DESCRIPTION OF THE INVENTION

Figure 1:
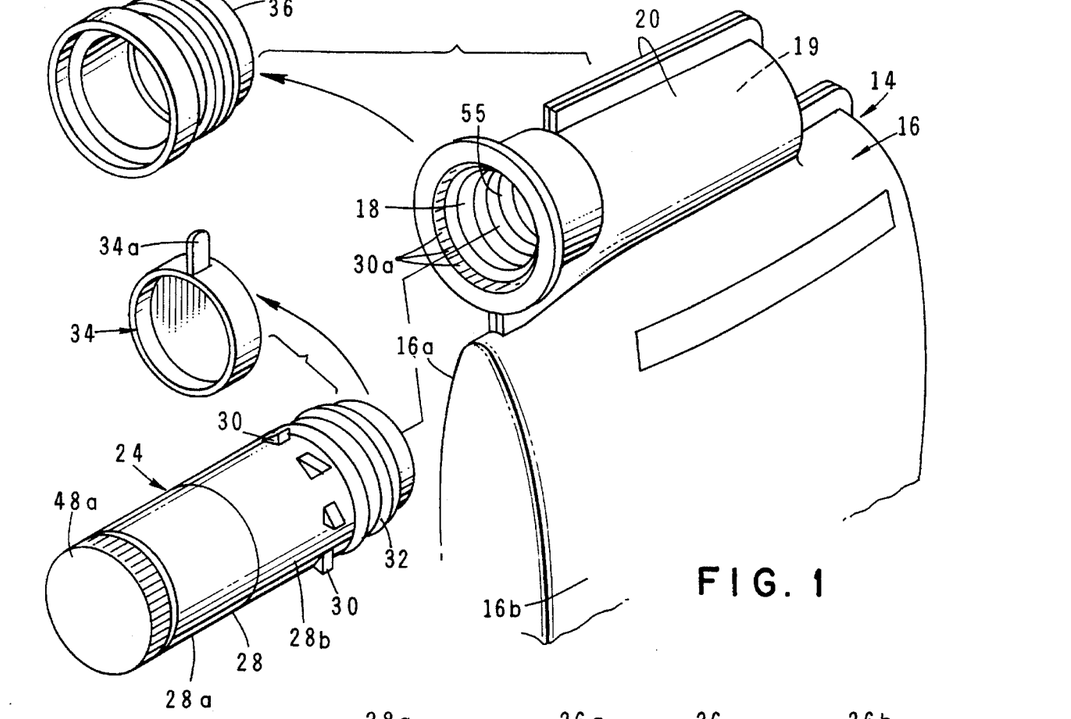
FIG. 1 is a generally perspective exploded view of one form of the apparatus of the present invention.
Figure 2:
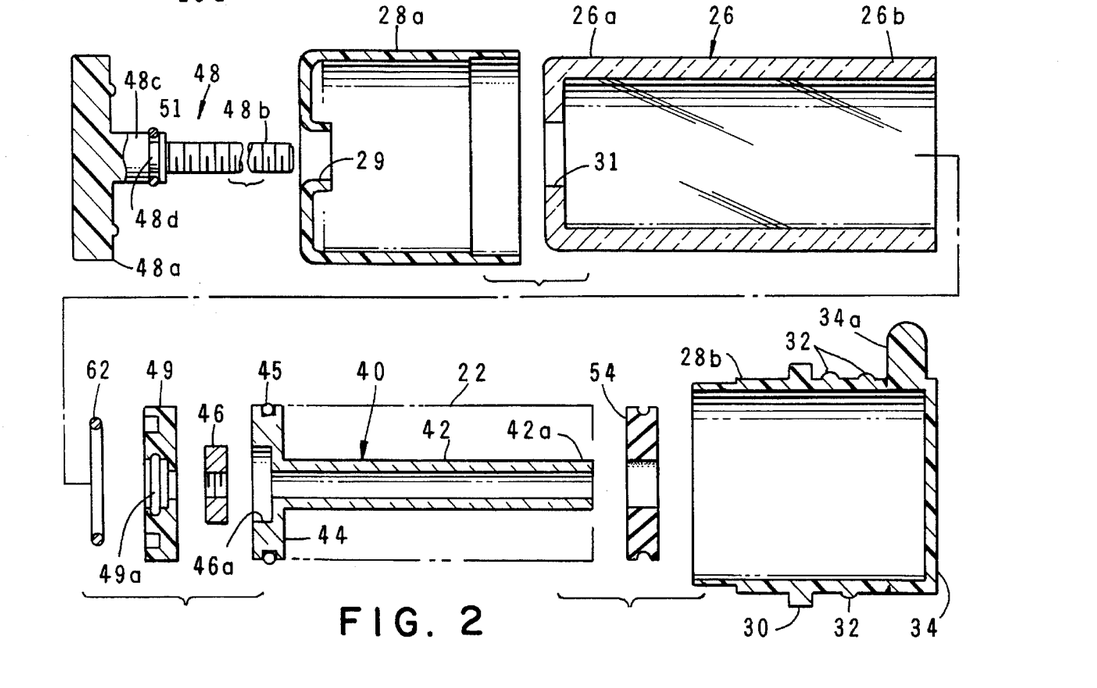
FIG. 2 is an enlarged front-elevation, cross-sectional exploded view of the vial assembly shown in FIG. 1.
Figures 3, 4, 5:
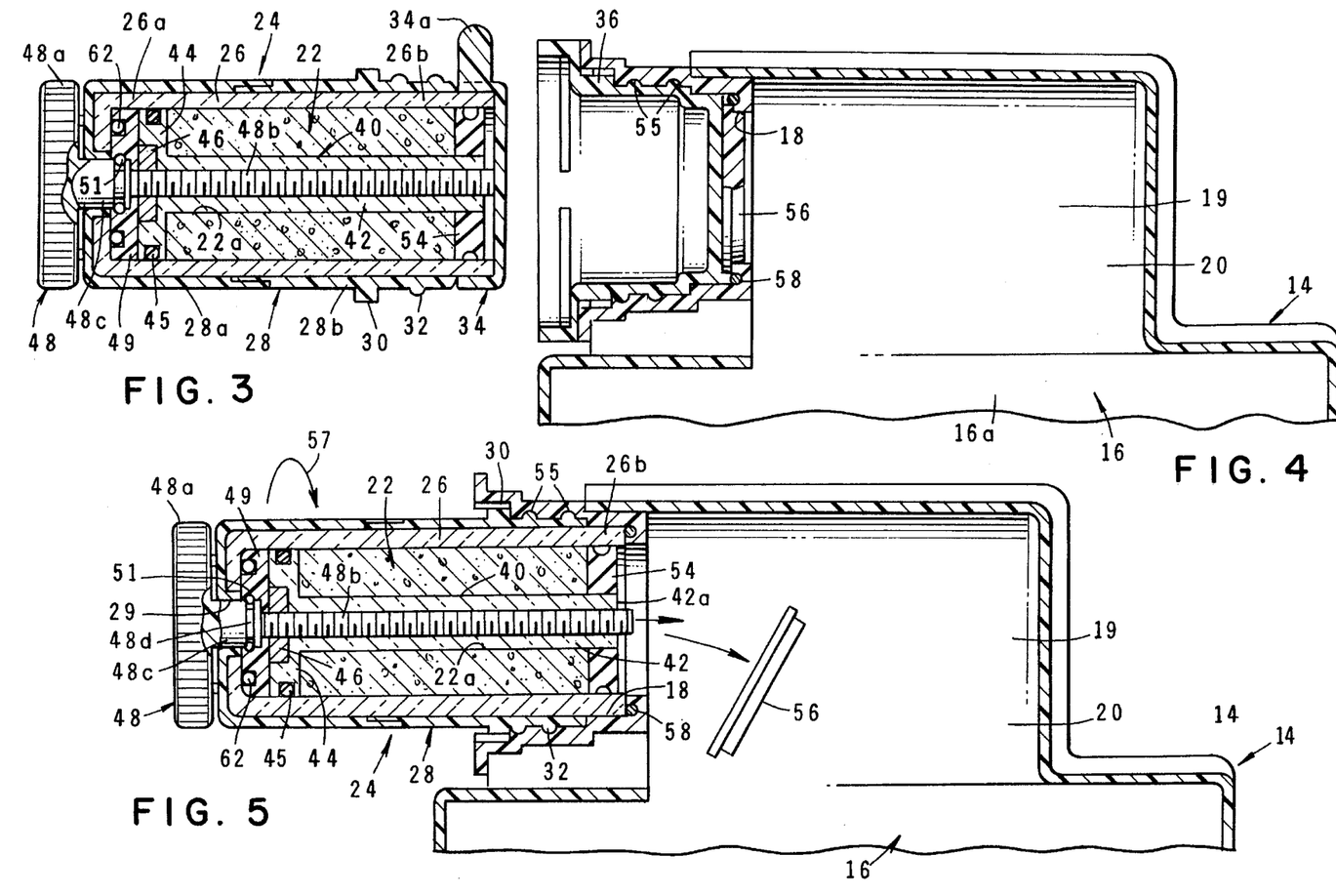
FIG. 3 is an enlarged, front-elevation, cross-sectional view of the vial assembly of FIG. 2 shown in an assembled configuration.
FIG. 4 is a fragmentary, cross-sectional view of the upper portion of the flexible bag assembly of the apparatus of this embodiment of the invention.
FIG. 5 is a fragmentary, front-elevation, cross-sectional view similar to FIGS. 3 and 4, but showing the drug vial assembly mated with the flexible bag assembly.

Referring now to the drawings and particularly to FIGS. 1 through 7, one form of the apparatus of the invention for controllably intermixing the first component with the second liquid component comprises a first container 14 having a fluid reservoir portion 16 for containing the second component and a side inlet port 18 formed in the upper portion of the container. Reservoir portion 16 is formed by sealably interconnected flexible walls 16a and 16b and inlet port 18 is formed at one end of a transversely extending, generally cylindrically shaped receiving chamber 19 which is superimposed over reservoir portion 16 and is in open communication therewith (FIG. 4). Walls 20, which cooperate to define the receiving chamber, are suitably interconnected with walls 16a and 16b to form a closable container.

The apparatus of the present invention also comprises adding means, of the character more fully defined in copending application, Ser. No. 07/989,097, which is incorporated herein by reference. The adding means functions to present the first component to the second component in a manner to permit intermixing the two components. In the embodiment of the invention shown in FIGS. 1 through 7, the adding means comprises support 22 (FIG. 3) upon which the first component is removably affixed. in one of the several ways described in Ser. No. 07/789,097. The adding means also includes a container assembly 24 for containing support 22 and a coupling means for coupling the container assembly 24 with inlet port 18. Container 14 is preferably constructed of flexible plastic sheets which are interconnected along their edges in a manner well known in the art to form the fluid reservoir. The receiving chamber preferably comprises a tubular shaped plastic structure which is superimposed over the reservoir and sealably connected to walls 16a and 16b in the manner shown in the drawings.

As best seen in FIGS. 2 and 3, container assembly 24 comprises a second container here shown as a glass vial 26 which is surrounded by a protective covering 28, such as a thin plastic cylinder made up of two cooperating portions 28a and 28b. Portion 28a of the protective covering covers the outboard end 26a of the glass vial while portion 28b covers the open end portion 26b of the glass vial. Provided on covering portion 28b are a plurality of circumferentially spaced locking teeth 30, the purpose of which will presently be described. Portion 28b of the covering is also provided with external threads 32 and includes a tear-off type portion closure 34 which can be removed from the glass vial assembly by pulling on the tear tab 34a. Similarly, inlet port 18 of flexible container 14 is initially sealed by a sterile closure 36 (FIGS. 1 and 4). These types of tear-away closures are of a character well known in the art. Portions 28a and 28b of the protective covering are stepped so that they can be conveniently joined together by any appropriate means such as adhesive or sonic bonding.

Also forming a part of the container assembly 24 of the invention is ejector means for ejecting support 22 from the glass vial and into the fluid reservoir 16. As best seen by referring to FIGS. 2 and 3, the ejector means here includes transfer means for moving support 22 within vial 26 from a first retracted position to a second extended position. The transfer means here comprises a support carrier 40 having an elongated stem portion 42 and an integrally formed, annular shaped hub portion 44. Hub portion 44 is provided with a circumferentially extending O-ring groove for receiving O-ring 45 and also includes a central counter-bore 44a within which an internally threaded ring-like member 46 is press fit. In a manner presently to be described, operator means controllably moves support 22 within vial 26 to its second position where it is ejected from the container assembly.

Figures 6, 7:
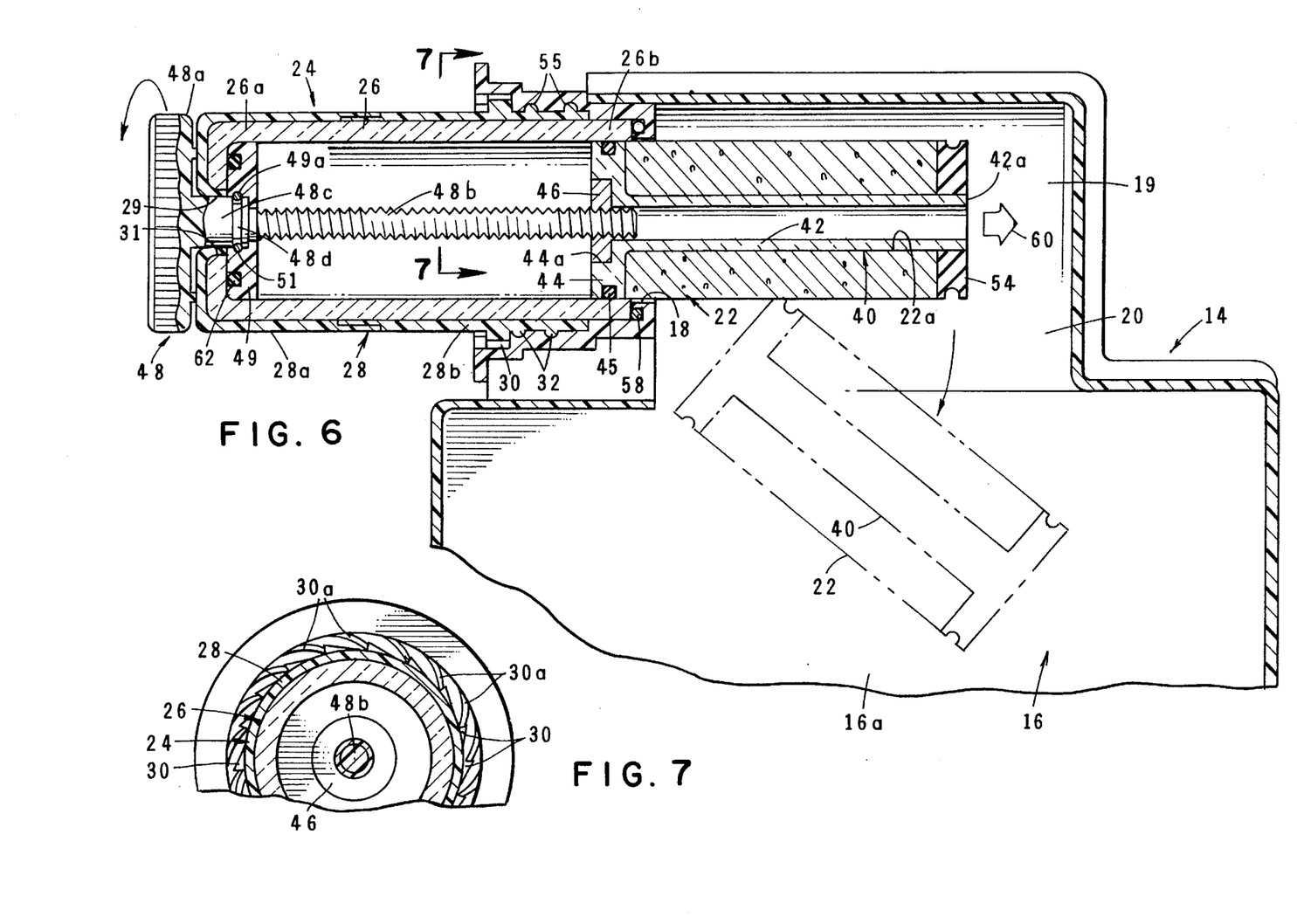
FIG. 6 is an enlarged, side-elevation, cross-sectional view of the apparatus of FIG. 5, but showing the adding means of the invention advanced into the interior of the flexible bag assembly.
FIG. 7 is a cross-sectional view taken along lines 7—7 of FIG. 6.

As shown in FIG. 2, the operator means here comprises an operator assembly 48 which includes a finger-engaging knob or handle 48a and an elongated, externally threaded stem 48b which is threadably receivable within ring 46. Operator assembly 48 is interconnected with the container assembly by a connector means which here comprises an annular disk 49 that is disposed proximate one end of vial 26. Disk 49 is interconnected with a collar portion 48c formed on knob 48a by means of a retainer ring 51 which is carried within groove 48d provided in collar portion 48b. As best seen in FIGS. 2 and 6, when the collar portion 48c is inserted through an opening 29 provided in cover 28 and through an aligned opening 31 provided in vial 26 it will be closely received into central bore of disk 49. As the parts mate, ring 51 will snap into a groove 49a provided in disk 49 thereby rotatably interconnecting the operator assembly with annular disk 49.

With the construction described in the preceding paragraph, rotation of knob 48a will cause disk 46 along with support carrier 40 to which it is connected to advance along threaded stem 48b in the manner shown in FIG. 6. As carrier 40 advances within vial 26, O-ring 45 will sealably slide along the internal surface of the vial as will an annular shaped rubber stopper 54 which is disposed proximate the inboard end 42a of stem 42 of carrier 40.

With the apparatus of the invention assembled in the manner shown in FIGS. 3 and 4, support 22 is sealably encapsulated within vial 26 between hub portion 44 of support carrier 40 and rubber stopper 54. As shown in the drawings, stem portion 42 of the carrier 40 extends through a central bore 22a provided in support 22 and functions to maintain the support centered within vial 26. Transfer assembly 48 is interconnected with retainer ring 49 in the manner previously described so that the threaded stem portion of the assembly extends longitudinally of stem 42 of the support carrier.

When it is desired to intermix the first component carried by support 22 with the second liquid component contained within reservoir 16 of the bag assembly, sterile closure 36 is removed from the inlet port of the bag assembly in the manner shown in FIG. 1 so as to expose internal threads 55 provided in the inlet port. Next, closure 34, which closes the open end of vial 26, is removed and discarded. The container assembly is then inserted into the inlet port 18 of the bag assembly in the manner shown in FIG. 5. As the container assembly is received within inlet port 18, threads 32 provided on the container assembly will mate with internal threads 55. Rotation of the container assembly in the direction of the arrow 57 shown in FIG. 5 will cause the assembly to advance within the inlet port 18 of the bag assembly. As the container assembly seats within the inlet port, a sterile cavity plug 56, which is normally disposed within inlet port 18, is ejected into the bag assembly in the manner shown in FIG. 5. Additionally, as the container assembly seats within inlet port 18, end 26a of vial 26 will sealably engage an O-ring 58 carried within inlet port 18 and locking teeth will engage flexible tabs 30a provided in inlet port 18 (FIGS. 1 and 7). Teeth 30 and tabs 30a are constructed so as to prevent removal of the vial assembly from the inlet port.

Figures 8, 9:
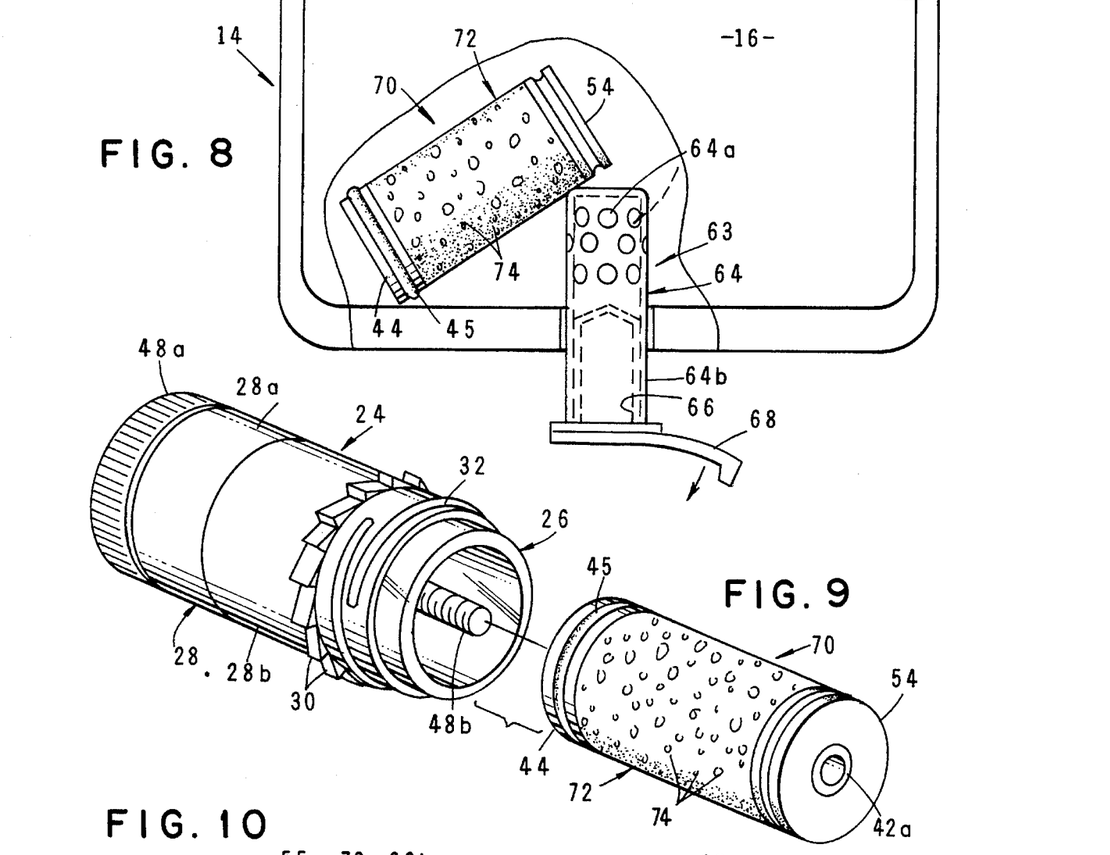
FIG. 8 is a front view of the bottom portion of the flex bag assembly partly broken away to show the position of an adding means disposed within the reservoir of the bag assembly.
FIG. 9 is a generally perspective, exploded view of an alternate from of drug vial assembly of the invention showing an adding means of the character illustrated in FIG. 8.

With the container assembly mated with the bag assembly in the manner shown in FIG. 5, the ejection means can be used to eject support 22 into the fluid reservoir 16 (FIG. 8). This is accomplished by rotating knob 48a in the direction of the arrow of FIG. 6. As knob 48a is rotated, internally threaded ring 46 will be caused to advance along threaded stem 48b in the manner shown in FIG. 6. This, of course, will result in the assemblage made up of the support carrier 40, the support 22, and the stopper 54 advancing into the receiving chamber of the bag assembly in the direction of the arrow 60 of FIG. 6. When the thus identified assemblage reaches the end of threaded stem 48b, the assemblage will fall by force of gravity into reservoir 16 in the manner indicated by the dotted lines in FIG. 6. It is to be noted that during the advancement of the support within vial 26 retainer disk 48 remains fixed proximate end 26a of the vial and is maintained in sealable engagement with the vial by an O-ring 62 which is carried by ring 49 in the manner shown in FIG. 6.

As shown in FIG. 8, a standpipe assembly 63 is provided proximate the bottom of the flexible bag or first container 14. The standpipe assembly includes a standpipe 64 having an aperture portion 64a extending upwardly into reservoir 16. The standpipe further includes a downwardly extending portion 64b terminating in an outlet 66 which is normally closed by a tear-off cap 68. As shown in FIG. 8, after the adding means has been ejected into the bag reservoir, it will rest against the standpipe in the manner shown so that the additive will be exposed to the liquid contained within reservoir 16 in an optimum manner.

Turning to FIG. 9, an alternate form of the adding means 70 of the invention, which is of the same character as shown in FIG. 8, is shown in association with container assembly 24. Container assembly 24 is of the same construction as previously described and includes a glass vial 26 which is surrounded by a protective covering 28.

Adding means 70 comprises a scaffold 72 which removably carries an additive 74. Scaffold 72, which is of a generally cylindrically shaped configuration, is constructed from a porous ceramic material into which selected additives and intermediate compounds have been removably affixed. Scaffold 72 can also be constructed from fused activated carbon particles, coated porous zirconium oxide bonded spherules, or other porous forms of polymer reactive supports.

Additive 74, which can be those described in Ser. No. 07/989,097, can be removably connected to, immobilized on, impregnated within or supported by the scaffold in a number of ways. The additives can be chemically or mechanically attached, affixed, or bound directly or indirectly, linked or cross linked, anchored to the surface of the scaffold or surface active agent or they can be absorbed, reaction catalyzed, electrostatically encapsulated, attached by chemical modification or transformation to the scaffold surface, polymerized on or through the scaffold with or without the use of an interpolymer, localized, entrapped, suspended, deposited, impregnated, coated, or occluded or otherwise removably affixed within voids, cells, tubules, and intersticies formed in the scaffold.

Figure 10:
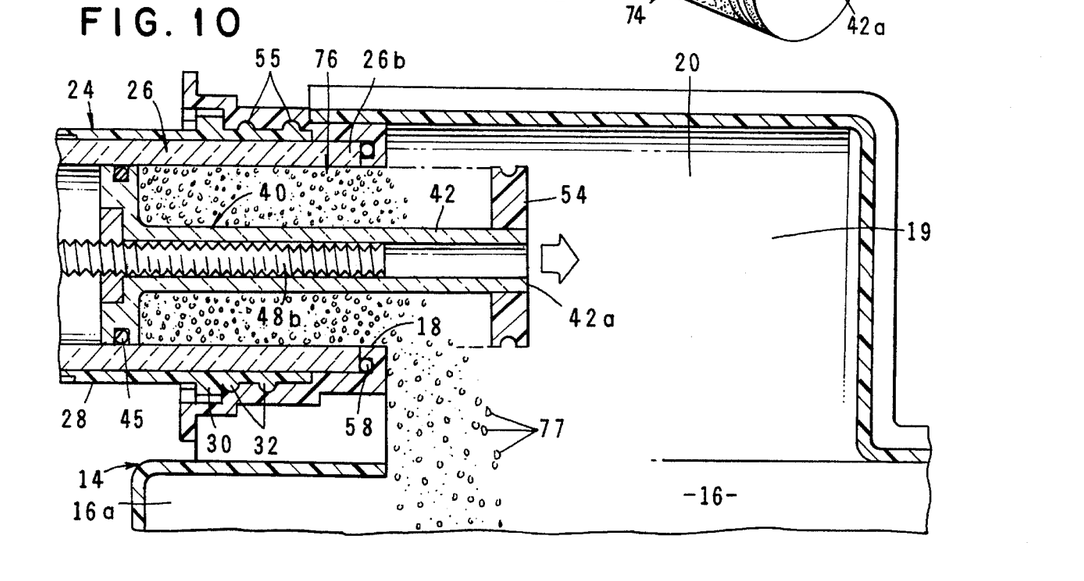
FIG. 10 is an enlarged front elevation, cross-sectional view of an alternate form of apparatus of the invention showing the additive being deposited within the reservoir of the flexible bag.
Figure 11:
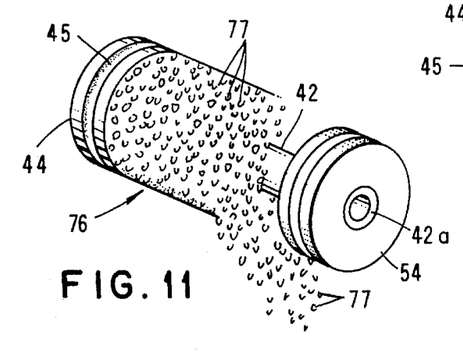
FIG. 11 is a generally perspective view of an adding means of the character shown in FIG. 10.

In FIGS. 10 and 11, still another form of adding means 76 of the invention is there illustrated. In FIG. 10 the adding means is shown mated with a flexible bag assembly, or container 14 of the character previously described herein. The additive of this latest form of adding means comprises a multiplicity of small particles or granules 77, which, through use of the ejection means of the invention, are controllably deposited into reservoir 16 by force of gravity. Granules 77 can be any number of different types of beneficial agents such as drugs, biologically active materials and various chemical elements and compounds.

When it is desired to intermix granules 77 with the second liquid component contained within reservoir 16 of the bag assembly, container assembly 24 is inserted into the inlet port 18. As the container assembly is received within inlet port 18, threads 32 provided on the container assembly will mate with internal threads 55. Rotation of the container assembly will cause the assembly to advance within the inlet port 18 of the bag assembly in the manner shown in FIG. 10. The ejection means, which is of the same character as previously described herein, is then used to advance the adding means to a position wherein granules 77 will fall by force of gravity into reservoir 16.

Figure 12:
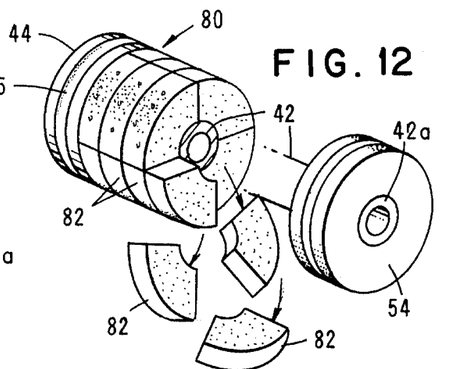
FIG. 12 is a generally perspective view of still another form of adding means of the invention.
Figure 13:
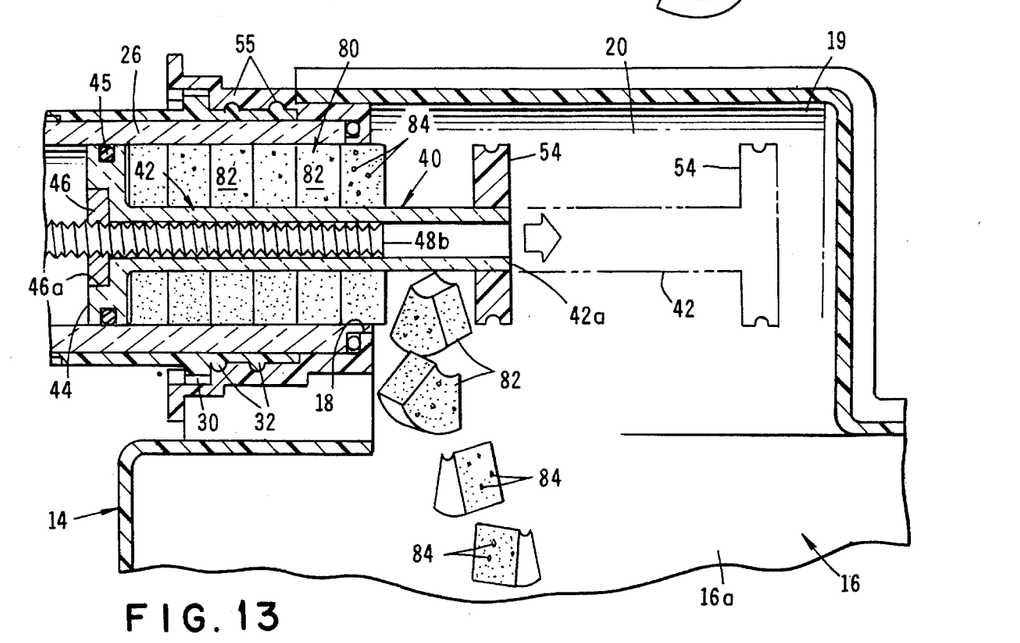
FIG. 13 is an enlarged front elevation, cross-sectional view of the apparatus of the invention showing the adding means of FIG. 12 being introduced into the upper portion of the flexible bag assembly.

In FIGS. 12 and 13, yet another form of adding means 80 of the invention is there illustrated. In FIG. 13 the adding means is shown mated with a flexible bag assembly, or container 14 of the character previously described herein. The adding means of this latest embodiment comprises a multiplicity of generally sector-shaped disks 82 which removably carry selected additives. Through use of the ejection means of the invention, the disks can be controllably deposited into reservoir 16 by force of gravity. Sector-shaped disks 82 comprise a scaffold to which any number of different types of beneficialagents 84 such as drugs, biologically active materials and various chemical elements and compounds can be removably connected.

When it is desired to intermix agents 84 with the second liquid component contained within reservoir 16 of the bag assembly, container assembly 24 is inserted into the inlet port 18 in the manner shown in FIG. 13. As the container assembly is received within inlet port 18, threads 32 provided on the container assembly will mate with internal threads 55. Rotation of the container assembly will cause the assembly to advance within the inlet port 18 of the bag assembly in the manner shown in FIG. 10. The ejection means, which is of the same character as previously described herein, is then used to advance the adding means to a position wherein disks 82 will fall by force of gravity into reservoir 16 (FIG. 13).

Figure 14:
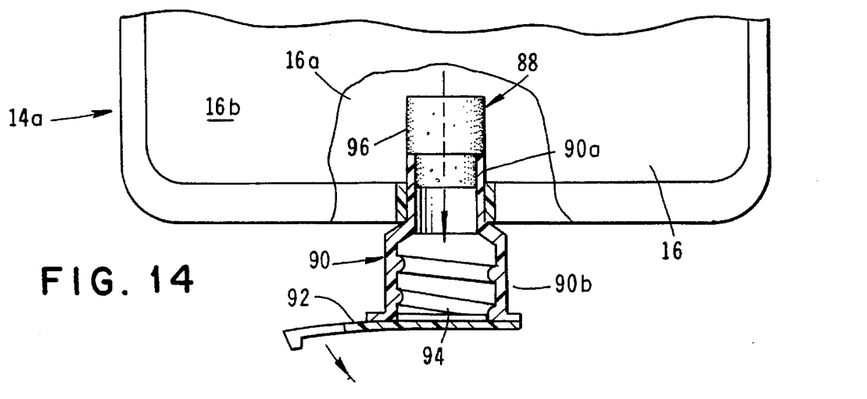
FIG. 14 is a front elevation view of the lower portion of an alternate form of flexible bag assembly partly broken away to show internal construction.

As shown in FIG. 14, a standpipe assembly 88 is provided in the bottom of reservoir 16 of the bag assembly 14. Assembly 88 is of a slightly different construction from that shown in FIG. 8 and here comprises a standpipe 90 having an upper portion 90a that extends into reservoir 16 and a lower, downwardly extending portion 90b. As before, a tear-away cap 92 closes the outlet port 94 of the standpipe. Carried within the upper portion 90a of the standpipe is a filtering means, or porous filter 96, which functions to filter out particulate matter that may form in reservoir 16 during the intermixing of the first and second components. Filter 96 can be constructed from various ceramics and similar types of porous materials of a character well known to those skilled in the art.

In using the apparatus of the invention shown in FIGS. 1 through 14, the fluid mixture formed in reservoir 16 as a result of the intermixing of the first and second components can be infused into the patient through the use of any suitable infusion set that can be interconnected with the outlet port of the standpipe assemblies 63 and 88 that are mounted proximate the bottom of the flexible bag assembly.

Figure 15:
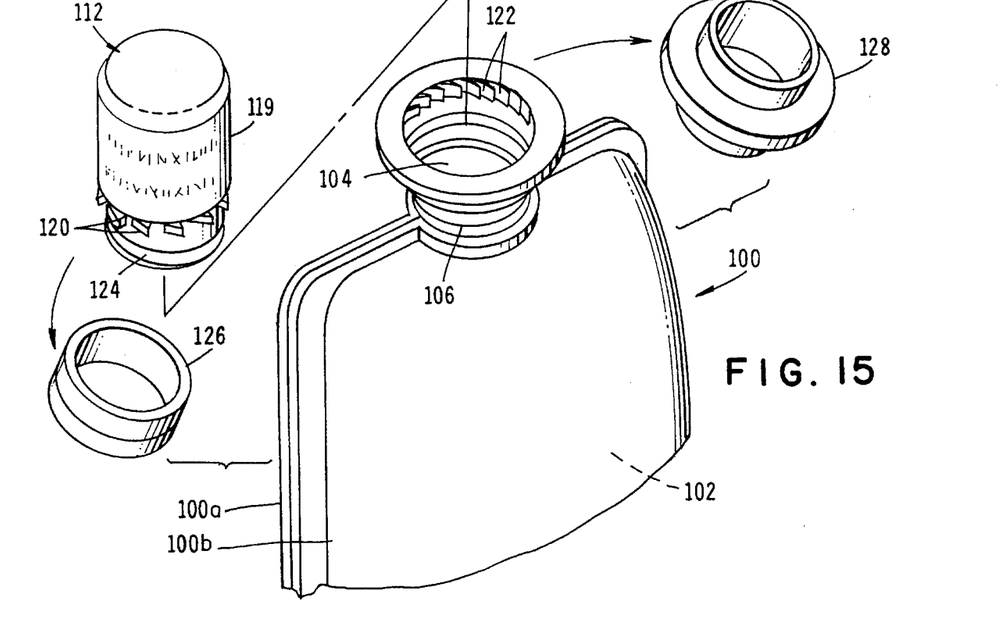
FIG. 15 is a generally perspective, exploded view of an alternate form of the apparatus of the invention.
Figure 16:
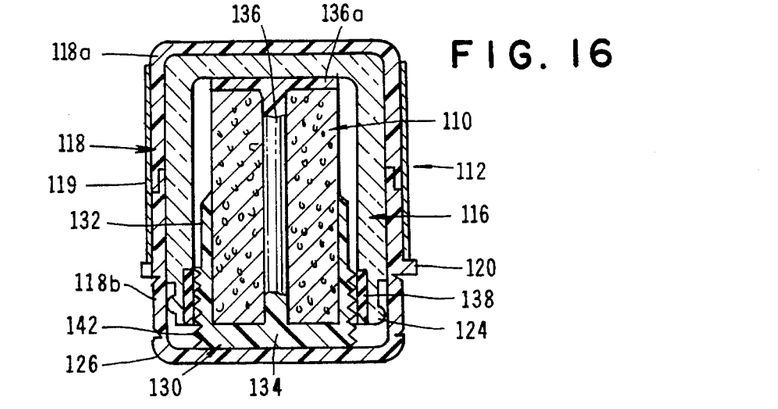
FIG. 16 is an enlarged, front-elevation, cross-sectional view of the vial portion of the apparatus shown in FIG. 15.
Figure 17:
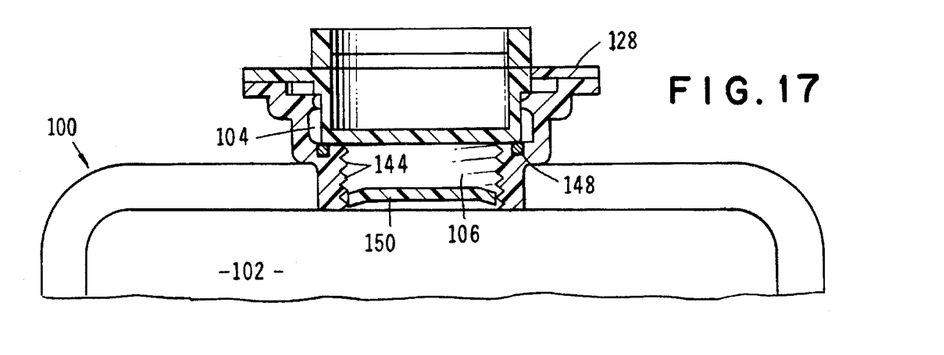
FIG. 17 is a front-elevation, cross-sectional view of the top portion of the flexible bag assembly of the form of the invention shown in FIG. 15.
Figure 18:
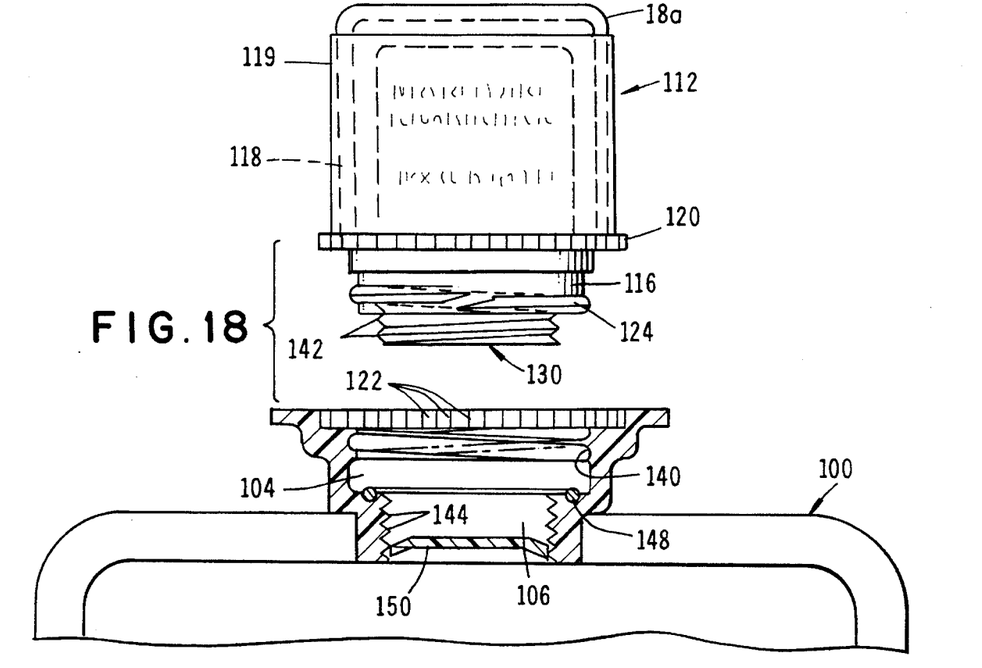
FIG. 18 is an exploded front view of the portion of the apparatus of the invention shown in FIG. 15.
Figure 19:
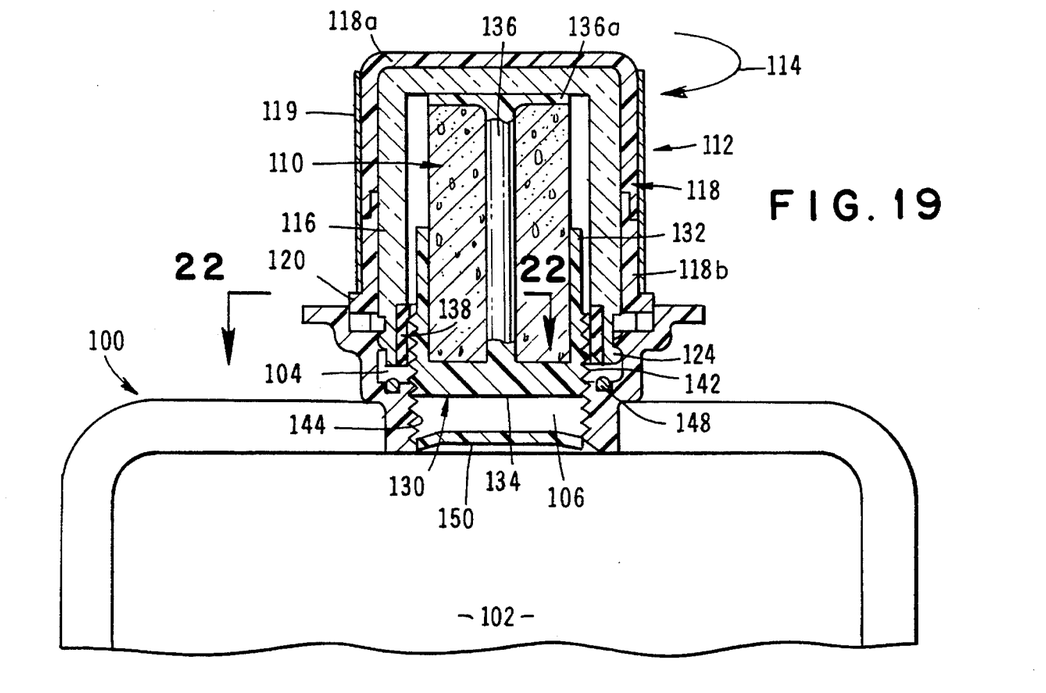
FIG. 19 is a front-elevation, cross-sectional view showing the drug vial assembly of the apparatus initially mated with the flexible bag assembly of this latest form of the invention.
Figure 20:
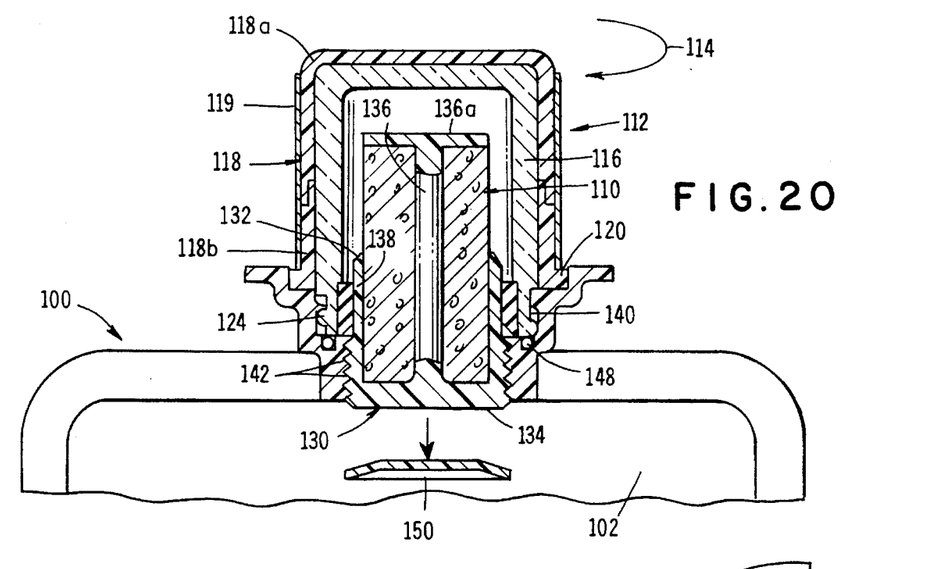
FIG. 20 is a front-elevation, cross-sectional view similar to FIG. 19 but showing the adding means of the invention having been advanced toward the reservoir of the flexible bag assembly.

Turning next to FIGS. 15 through 22, another embodiment of the invention is there shown. This latest embodiment comprises a first container 100 having a fluid reservoir portion 102 for containing the second component and a top inlet port 104 formed in the top of the container. Reservoir portion 102 is formed by sealably interconnected flexible walls 100a and 100b and inlet port 104 comprises a generally cylindrically shaped receiving chamber 106 which is superimposed over reservoir portion 102 and is in open communication therewith (FIG. 17). The inlet port which defines receiving chamber 106 is suitably interconnected with walls 100a and 100b to form a closable container.

The apparatus of the present form of the invention also comprises adding means which functions to present the first component to the second component in a manner to permit intermixing the two components. In this latest embodiment of the invention, the adding means comprises a support 110 (FIG. 16) upon which the first component is removably affixed in one of the several ways described in Ser. No. 07/789,097. The adding means also includes a container assembly 112 for containing support 110 and a coupling means for coupling the container assembly 112 with inlet port 104. Container 100 is preferably constructed of flexible plastic sheets which are interconnected along their edges in a manner well known in the art to form the fluid reservoir.

Figures 21, 22, 23:
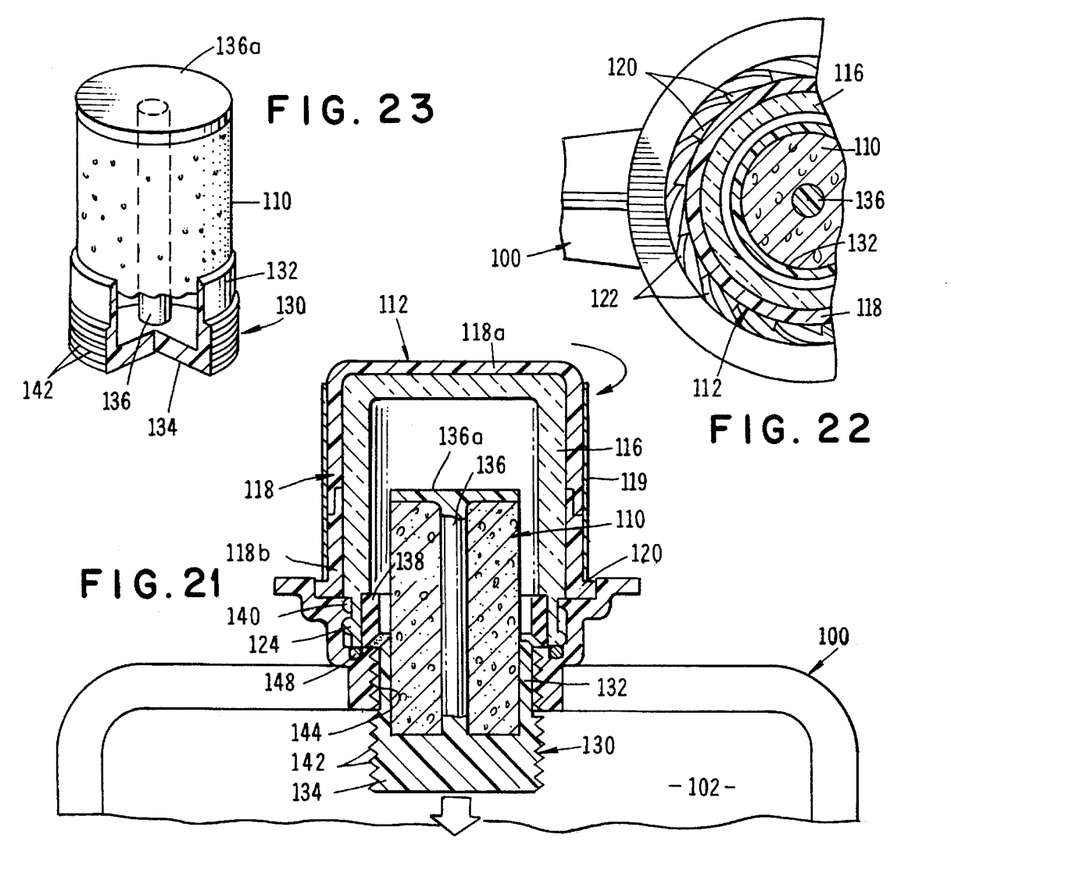
FIG. 21 is a front-elevation, cross-sectional view similar to FIG. 20 but showing further advancement of the adding means into the reservoir of the flexible bag assembly.
FIG. 22 is a cross-sectional view taken along lines 22—22 of FIG. 19.
FIG. 23 is a generally perspective view of the adding means of this latest form of the invention partly cut away to illustrate internal construction.

As best seen in FIG. 16, container assembly 112 comprises a second container here shown as a glass vial 116 which is surrounded by a protective covering 118, such as a thin plastic cylinder made up of two cooperating portions 118a and 118b. Portion 118a of the protective covering covers the closed end of the glass vial while portion 118b covers the open end of the glass vial. A medicament label 119 surrounds and interconnects portions 118a and 118b. Provided on covering portion 118b are a plurality of circumferentially spaced locking teeth 120 which lockably engage spaced locking tabs 122 provided within the inlet port structure (FIGS. 15 and 22). Portion 118b of the covering is also provided with external threads 124 and includes a tear-off closure 126 which can be removed from the glass vial assembly by pulling on the tear tab. Similarly, inlet port 104 of container assembly 100 is initially sealed by a sterile closure 128 (FIGS. 15 and 16). These types of tear away closures are of a character well known in the art. As before, portions 118a and 118b of the protective covering are stepped so that they can be conveniently joined together and held in position by the label 119.

Also forming a part of the container assembly 112 of the invention is ejector means for ejecting support 110 from the glass vial and into the fluid reservoir 102. As best seen by referring to FIGS. 21 and 23, the ejector means here includes transfer means for moving support 110 within vial 116 from a first retracted position to a second extended position. The transfer means here comprises support carrier 130 having an elongated stem portion 132 and an integrally formed, threaded base 134.

As best seen in FIG. 23, substrate 110 has a central bore which closely receives an integral stem 136 of the support carrier 130. Stem 136 includes a top plate 136a which engages the top of substrate 110. The support carrier includes a cylindrical wall, the upper portion of which circumscribes a portion of substrate 110 so that the substrate is held captive between base 134 and the top plate 136a. Wall portion 132 is in slidable frictional engagement with an inwardly, annular-shaped elastomeric ring 138 which forms a part of the operating means of this form of the invention. In a manner presently to be described, elastomeric ring 138 frictionally engages threaded portion 134 of the support carrier 130 during the ejection of the carrier from the second container. More particularly ring 138 is configured so that it will engage threaded portion 134 so that rotation of covering 118 and vial 116 will cause concomitant rotation of support carrier 130.

When it is desired to intermix the first component carried by support 130 with the second liquid component contained within reservoir 102 of the bag assembly, sterile closure 128 is removed from the inlet port of the bag assembly in the manner shown in FIG. 15. Next, closure 126, which closes the open end of vial 116 is also removed and discarded. The container assembly is then inserted into the inlet port 106 of the bag assembly in the manner shown in FIG. 19. As the container assembly is received within inlet port 106, threads 124 provided on container 116 will mate with interrupted internal threads 140 provided in inlet port 106. At the same time, threads 142 provided on support carrier 130 will engage threads 144 provided on the interior wall of the inlet port. Rotation of the container assembly in the direction of the arrow 114 shown in FIG. 19 will cause the assembly to advance within the inlet port of the bag assembly until vial 116 seats against an O-ring 148 provided proximate the inlet opening. Because of the novel design of the interrupted threads 124, after the container assembly has seated within the inlet port, the container assembly can continue to be rotated in the direction of the arrow 114. As the container assembly is rotated, elastomeric ring 138 will frictionally engage the threads on the support carrier causing the support carrier to rotate and controllably advance along threads 144 in the manner shown in FIG. 19 until the assemblage reaches the position shown in FIG. 21 where support 110, along with the carrier 130, will fall by force of gravity into reservoir 102. As the assemblage advances within the inlet port, a closure disk 150, which normally sealably closes the inlet to the reservoir will be dislodged in the manner shown in FIG. 20 and will fall into the reservoir. As the support carrying the first component is submerged into the liquid component contained in reservoir 102, the liquid in the reservoir will flow around, about and through support 110 causing efficient intermixture of the first and second components.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for controllably intermixing a first component and a second fluid component comprising:

(a) a first container having an inlet port and a fluid reservoir for containing the fluid component;

(b) adding means for presenting the first component to the fluid component for intermixing therewith, comprising a support upon which the first component is removably affixed;

(c) a second container assembly interconnectable with said inlet port of said first container, said container assembly including a second container for containing said support; and (d) ejection means for ejecting said support from said second container and into said fluid reservoir.

2. An apparatus as defined in claim 1 in which said ejection means comprises:

(a) transfer means for moving said support within said second container from a first retracted position to a second extended position; and (b) operator means connected to said transfer means for moving said support toward said second position.

3. An apparatus as defined in claim 2 in which said transfer means comprises a threaded member and in which said operator means comprises an operator rotatable relative to said threaded member.

4. An apparatus as defined in claim 3 in which said operator includes a handle portion and an elongated threaded stem threadably connected to said threaded member.

5. An apparatus as defined in claim 4 in which said ejector means further includes connector means disposed within said second container for interconnecting said operator with said container assembly.

6. An apparatus for controllably intermixing a first component and a second liquid component comprising:

(a) a first container having a top, a bottom and spaced-apart sides defining a fluid reservoir for containing the second liquid component, said container having an inlet port;

(b) adding means for presenting the first component to the second component for intermixing therewith, comprising a support upon which the first component is removably affixed;

(c) a container assembly adapted to be interconnected with said inlet port of said first container, said container assembly including a second container for containing said support; and (d) ejection means for ejecting said support from said second container said ejection means including transfer means connected to said support for moving said support within said second container.

7. An apparatus as defined in claim 6 in which said transfer means comprises a threaded member.

8. An apparatus as defined in claim 7 in which said ejection means further includes an operator rotatably connected to said container assembly, said operator including a handle portion and a threaded stem threadably connected to said threaded member.

9. An apparatus as defined in claim 7 in which said first component comprises a beneficial agent and in which said second component comprises a parenteral fluid.

10. An apparatus as defined in claim 7 in which said first component comprises a drug and in which said second component comprises a diluent.

11. An apparatus as defined in claim 7 in which said first component comprises a biologically active material.

12. An apparatus as defined in claim 7 in which said first component is removable from said support using affinity chromotography techniques.

13. An apparatus as defined in claim 7 in which said first component is connected to said support using azlactone functional compounds.

14. An apparatus as defined in claim 7 in which said first component comprises a multiplicity of granules of a beneficial agent.

15. An apparatus as defined in claim 7 in which said support comprises a multiplicity of generally sector-shaped forms.

16. An apparatus for controllably intermixing a first component and a second liquid component comprising:

(a) a first container having a top, a bottom and spaced-apart sides defining a fluid reservoir for containing the second liquid component, said container having an inlet port and an outlet port;

(b) adding means for presenting the first component to the second component for intermixing therewith, comprising a support upon which the first component is removably affixed;

(c) a container assembly adapted to be interconnected with said inlet port of said first container, said container assembly including a second container for containing said support; and (d) ejection means for ejecting said support from said second container said ejection means including transfer means connected to said support for moving said support within said second container to a position where said support will fall by force of gravity into said fluid reservoir.

17. An apparatus as defined in claim 16 in which said inlet port is located in one side of said first container.

18. An apparatus as defined in claim 16 in which said inlet port is located in the top of said first container.

19. An apparatus as defined in claim 16 further including a standpipe disposed in the bottom of said first container for engagement by said support upon said support falling into said reservoir.

20. An apparatus as defined in claim 19 further including filtering means mounted to said standpipe for filtering out particulates contained within fluid disposed within said reservoir.

* * * * *